United States Patent [19]
Egan et al.

[11] Patent Number: 5,141,852
[45] Date of Patent: Aug. 25, 1992

[54] ASSAY OF PROTEIN KINASES WITH PEPTIDE SUBSTRATES

[75] Inventors: John J. Egan, Silver Spring; Constantine Londos, Garrett Park, both of Md.

[73] Assignee: The United States of America as represented by the Department of Health and Human Services, Washington, D.C.

[21] Appl. No.: 282,562

[22] Filed: Dec. 12, 1988

[51] Int. Cl.$^5$ .................. C12Q 1/48; C07K 15/24
[52] U.S. Cl. ................................ 435/15; 435/21; 436/161; 530/327; 530/329; 530/344; 530/352
[58] Field of Search .................... 435/15, 21, 803; 530/328, 340, 344; 436/161, 178

[56] References Cited
PUBLICATIONS

Sofer and Britton *Biotechniques* 1:198-203, 1983.
Kemp et al. *Biochemistry* 73:1038-1042 1976.
House et al. *J. Biol. Chem.* 262:772-777, 1987.
Glass et al. *Anal. Biochem.* 87:566-575, 1978.

*Primary Examiner*—Sam Rosen
*Attorney, Agent, or Firm*—Birch, Stewart, Kolasch & Birch

[57] ABSTRACT

A method for assaying protein kinases that phosphorylate peptides such as Kemptide, such as cAMP-dependent protein kinase, or a glycogen synthase peptide, which is an excellent substrate for protein kinase C. Upon sequentially processing of reaction mixtures through tandem columns of cation and anion exchange resins improved separation of ATP from phosphorylated peptides is achieved such that radioactivity in background samples is nearly nil and the yield of phosphorylated peptides is high. This method is generally applicable to any protein kinase so long as the substrate peptide is appropriately structured such that the peptide retains a net positive charge when fully phosphorylated so that the peptide will adhere to the cation exchange resin and pass through the anion exchange resin. This method reduces labor, radioactivity, enzyme requirements, and costs of assaying protein kinases.

19 Claims, 2 Drawing Sheets

FIG.1A
Apply Sample
FIG.1B
Wash (optional)
FIG.1C
Elute $^{32}$P-Peptides with Acetic Acid
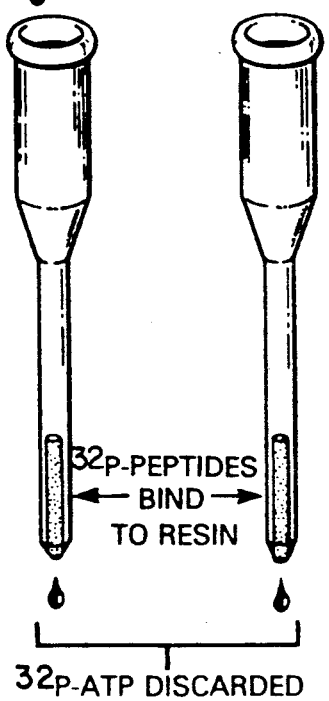
$^{32}$P-PEPTIDES BIND TO RESIN
$^{32}$P-ATP DISCARDED
RESIDUAL $^{32}$P-ATP TRAPPED
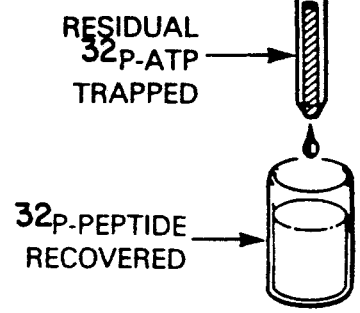
$^{32}$P-PEPTIDE RECOVERED

ASSAY OF PROTEIN KINASES WITH PEPTIDE SUBSTRATES

BACKGROUND OF THE INVENTION

1. Field of the Invention

The present invention is directed to a method for separating phosphopeptides from ATP which is useful for detecting protein kinase activities and specifically, to a chromatographic column method in which a stopped reaction mixture containing phosphopeptides and ATP is passed through a column containing a cation exchange resin and then through another column containing an anion exchange resin, and the eluate which contains phosphopeptides free from ATP is then recovered.

2. Description of Related Art

Protein kinases are a large class of biologically important molecules. Protein kinase activities are generally assayed by measuring the transfer of phosphate from $[\gamma\text{-}^{32}P]ATP$ to a substrate. The sensitivity of the assay relies on effective separation of the radiolabeled product from ATP. With a protein as the substrate, the phosphoprotein may be precipitated with acid, redissolved in base to remove trapped ATP, (D. A. Walsh et al, (1971) J. Biol. Chem. 246, 1977-1985), followed by reprecipitation with acid and trapping on paper filter disks, (E. M. Reimann et al, (1971) J. Biol. Chem. 246, 1986-1995), glass fiber filters, (J. Erlichman et al, (1971) Proc. Natl. Acad. Sci. USA 68, 731-735), or cellulose acetate filters (J. L. Goldstein et al (1973) J. Biol. Chem. 248, 6300-6307). Synthetic peptides have also been employed as protein kinase substrates. With the use of an anion exchange resin, one may achieve quantitative recovery of a phosphopeptide and effective separation of the phosphopeptide from the radioactive ATP (G. Tessmer et al (1973) Biochem. Biophys. Res. Commun. 50, 1-7; and B. E. Kemp et al, (1976) Proc. Natl. Acad. Sci. USA 73, 1038-1042). Another method involves trapping of phosphoproteins (J. J. Witt et al,. (1975) Anal. Biochem. 66, 253-258) and phosphopeptides (D. B. Glass et al. (1978) Anal. Biochem. 87, 566-575) on phosphocellulose paper under acidic conditions. ATP is removed more effectively with this phosphocellulose method in the presence of phosphoric acid (R. Roskoski (1983) in Methods in Enzymology (J. D. Corbin et al. Eds.). Vol. 99, pp. 3-6, Academic Press, New York).

Although the above procedures are well established for measuring protein kinase activities, all have certain drawbacks. First, the typical background in any of the published procedures is 0.04 to 0.1% of the initial radioactivity. Thus, under typical protein kinase assay conditions, with 1,000,000 cpm of $[\gamma\text{-}^{32}P]ATP$ in the reaction mixture, the background radioactivity in assay blanks is 400 to 1000 cpm of $^{32}P$. It is this background that determines sensitivity and dictates the amount of radioactive substrate and enzyme required for the detection of protein kinase activity. Second, all of the methods are somewhat tedious. It is therefore desirable to reduce both assay background and labor involved in assaying protein kinases.

SUMMARY OF THE INVENTION

Therefore, it is an object of the present invention to provide a protein kinase assay method in which substrates are completely separated from the radioactive ATP in order to produce a high signal-to-noise ratio.

It is a further object of the present invention to provide a method which reduces expense in assaying protein kinases by requiring less radioactive ATP.

It is yet a further object of the present invention to provide a method in which $^{32}P$-phosphorylated synthetic peptides are quantitatively recovered with little or no background radioactivity.

It is still a further object of the present invention to provide a method in which the processing of samples requires minimum labor.

It is another object of the present invention to provide a method for measuring protein kinase activities by separating phosphorylated peptides from ATP.

It is yet another object of the present invention to provide a method for measuring protein kinase activities which is effective with synthetic substrates for both cAMP-dependent protein kinase (A-kinase) and protein kinase C (C-kinase).

It is still another object of the present invention to provide a protein kinase assay method in which exposure of the investigator to the radioactive ATP is greatly reduced.

The foregoing objects and others are accomplished in accordance with the present invention, generally speaking, by providing a method for separating phosphopeptides from ATP in order to measure protein kinase activity comprising the steps of (a) adding an amount of washing solution to a stopped reaction mixture of a majority of ATP and phosphopeptides so as to form a prepared solution; (b) adding said prepared solution into a first column containing a cation exchange resin so as to retain said phosphopeptides in said first column and remove ATP; (c) adding an effective amount of an elution acid to said first column and collecting from said first column a first eluate of said phosphopeptides; (d) passing said first eluate through a second column containing an anion exchange resin so as to trap residual ATP and collecting from said second column a second eluate which contains said phosphopeptides which are free from ATP. Optionally, a second amount of washing solution may be added to the first column after step (b) so as to remove further ATP.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is further illustrated in the accompany drawings wherein:

FIGS. 1A, 1B and 1C illustrates the general chromatographic scheme for separating ATP from phosphopeptides.

DETAILED DESCRIPTION OF THE INVENTION

Figure 2A:
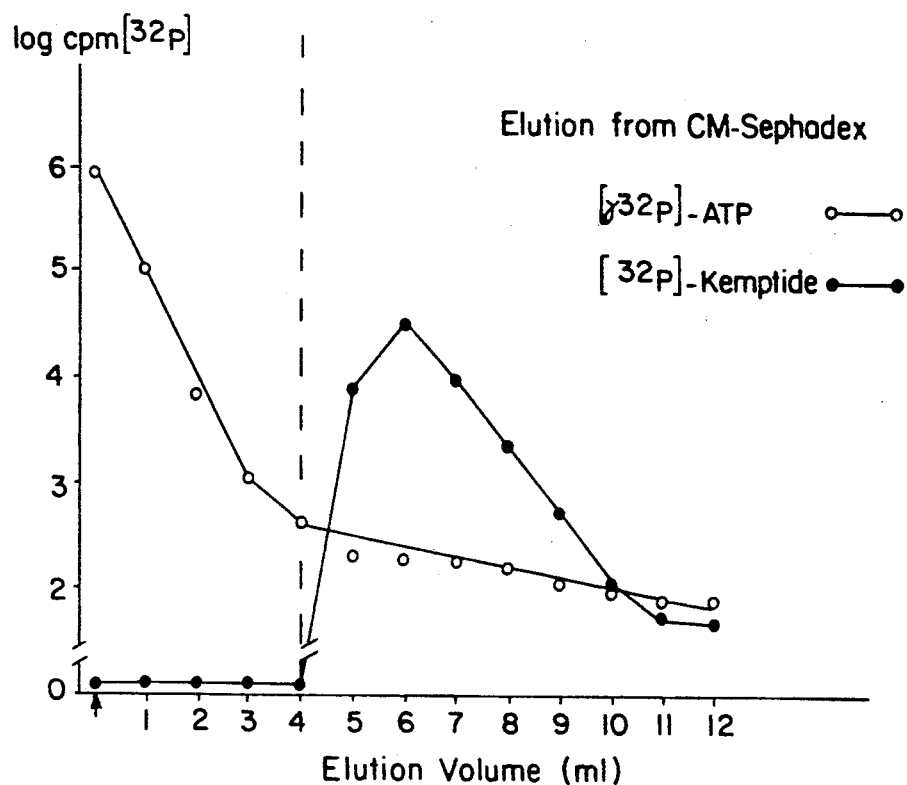
FIGS. 2A and 2B show the elution profiles of test compounds such as $[\gamma\text{-}^{32}P]ATP$ and $[^{32}P]$-Kemptide, through the tandem column procedure.

The general chromatographic scheme for separating ATP from phosphopeptides is shown in FIG. 1 which outlines a procedure for the processing of either A-kinase or C-kinase assays for example. The eluates from Steps A and B are discarded, while the eluates from Step C are collected in liquid scintillation (LS) vials. Depending on the purity of the protein kinase sample tested, any of a number of elution procedures may be employed in this method. The method of the present invention is generally applicable to any protein kinase so long as the substrate peptide is appropriately structured such that the peptide retains a net positive charge when fully phosphorylated so that the peptide will adhere to the cation exchange resin and pass through the anion exchange resin.

In general, a volume of the ATP washing solution is added to a stopped reaction mix containing the phosphorylated peptide and ATP, and the contents are poured into a first column containing a cation exchange resin such as CM-Sephadex (Step A). The stopped reaction mix is boiled if extraordinarily high amounts of protein are present, before the washing solution is added. The washing solution contains a sufficient amount of ATP so as to provide a two-fold purpose for (i) effective displacement of radioactive $[\gamma\text{-}^{32}P]ATP$, and (ii) with respect to the pH of the solution, to allow for quantitative binding of $^{32}P$-peptide to the cation exchange resin (lower pH limit) and for chemical compatibility of the cation exchange resin within the pH range (upper pH limit) and has a concentration of ATP from about 0.5 mM to 5.0 mM and a pH of about 6.0 to 8.0. For example, an ATP washing solution of about 5 mM ATP with a pH of about 6.8 may be used. The cation exchange resin employed in the first column may be a cross-linked polymer and may be in the form of beads having a bead size in the range of 120 $\mu$m, and preferably in the range of about 40–120 $\mu$m depending upon the packing properties desired of the cation exchange resin which will determine the flow rate of liquid through the resin. Cation exchange resins useful in the method of the present invention include resins which bind to phosphorylated peptides but not to ATP, such as CM-Sephadex, and any other resin which contains an ionizable, reactive-group which has as its property a pK of 3.5 to 4.0, as does the carboxy-group of CM-Sephadex, such that the peptide, which binds to the reactive-group, is displaced (exchanged) upon eluting the resin with any acid, the pH of which is lower than that of the pK of the reactive group. CM-Sephadex is a carboxymethyl derivative of Sephadex which is a bead-formed, cross-linked dextran gel which swells in water and aqueous salt solution. Such resin must not irreversibly (permanently) bind the peptide, and such acid must not be chemically incompatible with the matrix or reactive group of such resin. It follows that such acid must not be chemically incompatible with the second resin, over which the acid eluate must flow (for the purpose of binding ATP). Preferably CM-Sephadex may be used.

The eluate from step A, containing most of the ATP, is discarded, after which the first column may optionally be washed again with a volume of the ATP washing solution, and the eluate again discarded (Step B). This step is optional but reduces background values with kinase samples which contain high concentrations of proteins.

The first column, containing the phosphorylated peptides bound to the ion exchange resin, is mounted atop a second column which contains an anion exchange resin, such as Dowex AG1-X8, and a volume of an elution acid, such as acetic acid, is then added to the first column (Step C). The eluate from the first column passes directly through the second column and into a recovery means, such as a scintillation vial. The anion exchange resin employed in the second column is a resin suitable for trapping residual ATP and allowing phosphorylated peptides to pass thereover, such as Dowex AG1-X8, and any other resins which contain an ionizable group that will in the presence of the acid, permit quantitative binding of the negatively-charged phosphates of ATP, and permit the net positively-charged peptide (which contains a net positive charge when fully phosphorylated and when in the presence of any acid employed in elution from the cation exchange resin, above) to quantitatively elute from the anion exchange resin. Dowex AG1-X8 is a strongly basic anion exchanger and more specifically an 8% cross-linked styrene-divinylbenzene matrix for separating inorganic and organic anions. Such resin must not be incompatible with the acid employed in the elution from the first column, and such resin must not irreversibly (permanently) bind the peptide. Also, with respect to any acid employed in elution from either of the resins (cation- or anion-exchange resins) such acid must not be incompatible with the chemical scintillant vehicle, which is used in the process of liquid scintillation which follows the assay and permits measurement of radioactivity. The resin may have a size in the range of 200 mesh and preferably in the range of about 100–200 mesh depending upon the packing properties desired of the anion exchange resin, which will determine the flow rate through the resin. The elution acid used in Step C is an acid suitable for extracting the phosphorylated peptides from the cation exchange resin and allowing for residual ATP to be trapped in the anion exchange resin. Suitable elution acids include for example acetic acid, which is employed because it is (1) compatible with both the cation and anion exchange resins, (2) allows for quantitative elution of peptide from the cation exchange resin, (3) allows for quantitative binding of ATP to the anion exchange resin, (4) allows for quantitative elution of peptide through the anion exchange resin, and (5) does not interfere with the scintillation chemicals employed in the liquid scintillation measurement of radioactivity. Any acid employed other than acetic acid must adhere to these properties and need not be an organic acid.

EXAMPLES

The procedures presented below are especially useful for relatively pure protein kinases and relatively crude fat cell extracts.

Materials. ATP, cAMP, CM-Sephadex cation exchange resin, bead size 40–120 $\mu$m (C-25-120), dithiothreitol (DTT), A-kinase inhibitor (PKI), Kemptide (synthetic heptapeptide substrate for A-kinase, H$_2$N-Leu-Arg-Arg-Ala-Ser-Leu-Gly-COOH), Mops (3-[N-Morpholino]propanesulfonic acid (free acid)), sodium dodecyl sulfate (SDS), histone H1, and Tris were obtained from Sigma Chemical Co. The ATP used in bulk eluting solutions was the least expensive grade (Sigma, No. 3377), prepared by phosphorylation of adenosine. Bovine brain phosphatidylserine and 1,2-diolein were from Avanti Polar Lipids, Inc. (Birmingham, Ala.). Dowex AG1-X8 anion exchange resin (100–200 mesh) was from Bio-Rad Laboratories (Richmond, Calif.). $[\gamma\text{-}^{32}P]ATP$ (10–25 Ci/mmol) was from either International Chemical and Nuclear Corp. (Irvine, Calif.) or New England Nuclear (Boston, Mass.). The C-kinase dodecapeptide substrate (C. House et al, (1987) J. Biol. Chem. 262, 772–777), GS-peptide, i.e. H$_2$N-Pro-Leu- Ser-Arg-Thr-Leu-Ser-Val-Ala-Ala-Lys-Lys-COOH, was a gift from Dr. Bruce E. Kemp (Department of Medicine, University of Melbourne, Repatriation General Hospital, Heidelberg, Australia).

Preparation, regeneration, and storage of chromatographic columns. CM-Sephadex cation exchange resin was hydrated in $H_2O$, the fines were decanted, and 2 ml of a 1:1 suspension was introduced into glass columns fitted with glass wool plugs. The following procedure permits rapid and accurate distribution of resins to columns. Two-milliliter aliquots of a vigorously stirring 50% resin suspension are rapidly transferred to the columns with a 2-ml plastic pipet linked with flexible tubing to a Becton-Dickinson Cornwall continuous pipettor. The tip of the plastic pipet is removed to increase the size of the opening. Columns were charged with 8 ml of 30% acetic acid followed by 8 ml of $H_2O$. For storage between experiments, the columns were washed with 10 ml of 0.02% $NaN_3$ in $H_2O$ to prevent microbial growth. Regeneration of columns prior to each processing cycle was performed with 8 ml of 30% acetic acid followed by 8 ml of $H_2O$. After those experiments in which the protein kinase samples contained extraordinarily large amounts of protein, the columns were washed once with 5 ml of 1 M NaCl before regeneration for the next assay.

Occasionally, porosity developed in the CM-Sephadex resin bed, resulting in reduced column flow rates. This problem was eliminated by adding $H_2O$ and stirring the resin bed with a wood applicator. Columns which had not been used for a prolonged period of time and manner. One day before they were to be used, the CM-Sephadex columns were washed with 8 ml of 30% acetic acid, followed 1-2 h later by 8 ml of $H_2O$. The resin bed was stirred with a wooden applicator and the columns were allowed to drain. The columns were again washed with 8 ml of $H_2O$. The day they were to be used, the columns were regenerated as above with acetic acid followed by $H_2O$, and, after the columns had drained, the column resin was packed by tamping the column rack on a bench top four or five times. Proper rehydration of the CM Sephadex resin was essential for optimal peptide recovery. However, as column performance was not altered by repeated drying and rehydrating over the course of many months, it was not necessary to store the resin under hydrated conditions.

The Dowex AG1-X8 anion exchange resin (100-200 mesh) was washed three times with $H_2O$ followed by 5 bed vol each of 1 N NaOH, glacial acetic acid, and 30% acetic acid. Two milliliters of a 50% suspension of resin in 30% acetic acid were introduced into glass columns fitted with glass wool plugs. At the completion of each experiment, the resin was washed with 8 ml of 30% acetic acid. Columns treated in this manner were ready for the next experiment. For experiments in which the protein kinase samples contained a large amount of protein, the resin was washed with 5 ml of 3 N NaOH prior to washing with acetic acid. Following prolonged storage, the columns were prepared for reuse by washing with 30% acetic acid (1-2 ml) and stirring with a wooden applicator to remove porosity in the resin for reasons described above. As with the CM-Sephadex columns, the Dowex AG1-X8 columns were unaffected by repeated drying and rehydrating between experiments.

Glass columns, identical to those used in the tandem-column adenylate cyclase assay method (Y. Salomon et al (1974) Anal. Biochem. 58, 541-548), were used for both resins. The columns were 21 cm in length and the internal diameter of the stem portion was 0.7 cm. The columns were arranged in identical racks, accommodating 50 columns each, which may be stacked one atop the other, and matching trays holding 50 scintillation vials were used to collect the final eluates.

Assay of protein kinase activities. All protein kinase assays were conducted in 13×100-mm glass test tubes. The assay of A-kinase was performed with 100 um Kemptide, 20 mM Mops, pH 7.0, 16 mM magnesium acetate, 100 μM ATP, 4 mM DTT, 0.5 μCi[$\gamma$-$^{32}$P]ATP, and, where indicated, 16 μM cAMP. With the reaction tubes in a 4° C. ice bath, the assay ingredients were added to give a total volume of 60 μl, and the reaction was initiated by transferring the rack of reaction tubes to a 30° C. bath. At the times indicated in the description of FIG. 2 and in the Tables, the reaction was stopped by transferring the rack of tubes to the 4° C. ice bath and 20 μl of a stopping solution was added quickly with a Hamilton repeating syringe. The stopping solution contained 100 mM ATP, pH 7.0, and where removal of free magnesium was desired, 100 mM EDTA was included. Also, for reactions containing large amounts of bovine serum albumin (BSA), such as adipocyte extracts, the 20-μl stopping solution also contained 250 mM DTT and 5% SDS, pH 7.0. Samples were kept in the ice bath until the completion of the experiment. For experiments in which the enzyme samples contained extraordinarily high protein concentrations, the rack containing the reaction tubes was immersed in a boiling $H_2O$ bath for 2 min.

A-Kinase sources were the cytosolic extracts of rat adipocyte homogenates, prepared as described by Honnor et al (R. C. Honnor et al (1985) J. Biol. Chem. 260, 15122-15129), the commercial catalytic subunit, and partially purified holoenzyme prepared according to Beavo et al (J. A. Beavo et al (1974) in Methods in Enzymology (K. Moldave and L. Grossman Eds.), Vol. 30(C), pp. 299-308, Academic Press, New York). Under the above assay conditions, greater than 95% of Kemptide phosphorylation by these enzyme samples was attributable to A-kinase as assessed by either cAMP activation or inhibition by the specific inhibitor of this protein kinase (C. D. Ashby et al (1972), J. Biol. Chem. 247, 6637-6642), or by both criteria with adipocyte preparations.

The C-kinase reaction mixture contained 20 uM GS-peptide, 10 mM Tris-HCl, pH 7.5, 5 mM magnesium acetate, 20 μM ATP, 0.5 mM $CaCl_2$, and 0.5 μCi[$\gamma$-$^{32}$P]ATP, in a total volume of 100 μl. Where indicated, lipids were added to give final concentrations of 100 μg/ml of phosphatidylserine and 10 μg/ml of diolein. The lipid mixture was prepared by sonication in 20 mM Tris-HCl, pH 7.5, for 1 min at 30° C. The reaction was initiated by the addition of approximately 10 mU of C-kinase and stopped as described above for the A-kinase reaction. Highly purified C-kinase from rat brain (K. P. Huang et al (1986), J. Biol. Chem. 261, 12134-12140) was a gift from Dr. Kuo-Ping Huang, National Institutes of Health.

Preparation of phosphopeptides. In order to follow the elution pattern of phosphopeptides over the chromatographic columns, $^{32}$P-labeled peptides were prepared and purified. Under the assay conditions described above, 20 U of the commercial catalytic subunit of A-kinase were reacted with 10 uM Kemptide and 5 μM [$\gamma^{32}$P]ATP for 60 min. [$^{32}$p]Kemptide was separated from ATP by two passages through a Dowex AGl-X8 column (B. E. Kemp et al (1976), Proc. Natl. Acad. Sci. USA 73, 1038–1042), and the purified material bound quantitatively to P-81 phosphocellulose paper. Phosphorylated GS-peptide was prepared by reacting 10 mU of purified C-kinase with 20 μM [γ$^{32}$P]ATP and 20 μM peptide for 30 min. The phosphorylated peptide, which was purified by the method used to purify the phosphorylated Kemptide, also bound quantitatively to phosphocellulose paper.

Figure 2B:
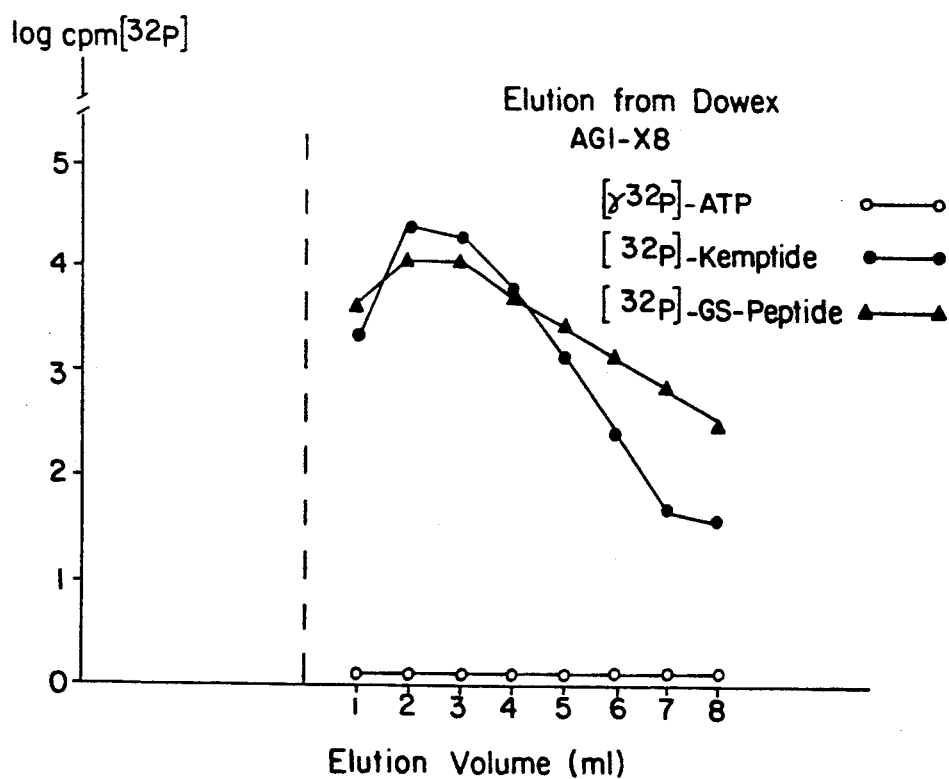

FIG. 2 shows the elution profiles of test compounds, such as [γ-$^{32}$P]ATP and [$^{32}$P]-Kemptide, through the tandem column procedure of the present invention. Elution of compounds from the CM-Sephadex column are shown to the left of the vertical line in the figure, while elutions from both the CM-Sephadex and the AGl-X8 columns are shown to the right of the vertical line. FIG. 2A to the right of the vertical line shows materials emerging from the CM-Sephadex column and destined to pass through the AGl-X8 column, while FIG. 2B shows the materials that emerge from the AGl-X8 column. Note the log scale of the ordinate in FIG. 2. For illustrative purposes, 1 ml of the ATP washing solution was added to the stopped reaction mix, and the contents of the reaction tube were applied directly onto the resin bed with a Pasteur pipet. (Typically, as described below, the reaction tube contents, usually 5 ml, are merely poured into the column, which broadens the radioactivity peaks but does not increase background values.) The elution of radioactive materials with successive 1-ml aliquots of the ATP washing solution is shown. Upon emergence of the fourth milliliter of washing solution, approximately 99% of the radioactive ATP was eluted, while all of the [$^{32}$P]Kemptide remained bound. Again, for illustrative purposes, FIG. 2 depicts the elution of [$^{32}$P]ATP and [$^{32}$P]Kemptide from the CM-Sephadex column with successive 1-ml aliquots of 30% acetic acid before (FIG. 2A) and after (FIG. 2B) passage through the Dowex AGl-X8 column. The acetic acid continued to remove radiolabeled ATP and quantitatively eluted the [$^{32}$P]Kemptide from the CM-Sephadex column. Upon passage of the acetic acid eluate through the AGl-X8 column, all residual ATP was trapped in the resin, while the [$^{32}$P]Kemptide passed through the AGl-X8 resin. In assays lacking a large amount of extraneous protein, the amount of [$^{32}$P]ATP that passed through the Dowex resin was barely discernible above the background counting rate of the scintillation counter. In all cases, the recovery of [$^{32}$P]Kemptide was at least 95% of that which was applied initially to the CM-Sephadex column. FIG. 2B also shows the elution profile of [$^{32}$P]GS-peptide which was applied and eluted under conditions identical to those described above for the [$^{32}$P]Kemptide. Again, recovery of the radiolabeled GS-peptide was greater than 95% of that which was applied initially to the CM-Sephadex column.

The general elution method according to the present invention advantageously reduces labor in assaying protein kinases and may be employed generally as follows. A volume of the ATP washing solution, usually 5 ml, is added to the stopped protein kinase reaction mixture with a repeating syringe; this addition is performed with sufficient vigor to mix the stopped reaction mixture into the ATP washing solution. The contents are poured into the CM-Sephadex column and the tubes are permitted to drain for a few minutes while resting inverted in the bowl portion of the columns. After the liquid has drained from the CM-Sephadex resin, these columns are mounted over the Dowex AGl-X8 columns. Eight milliliters of 30% acetic acid is applied to the CM-Sephadex columns and the total eluate from the AGl-X8 columns is collected in scintillation vials. In such an elution scheme, somewhat more radioactive ATP is carried through to the Dowex AGl-X8 resin than in the elution scheme depicted in FIG. 2 but, again, little ATP passes into the scintillation vial. Typically (Table 1), in this rapid elution method, fewer than 10 cpm of $^{32}$P from the nucleotide elutes from the Dowex AGl-X8 column, an assay background value which is barely discernible above the machine background counting value, 14 cpm, of the scintillation counter used in these experiments. However, nearly all (>94%) of the [$^{32}$P]Kemptide or [$^{32}$P]GS-peptide is recovered (Table 2). Also, although 5 mM ATP was used in the bulk eluting solutions for the experiments presented in this paper, we have found that lowering the ATP to 0.5 mM does not change the column performance.

TABLE 1

MEASUREMENT OF PROTEIN KINASE ACTIVITIES IN RAT ADIPOCYTE EXTRACTS WITH KEMPTIDE AND GS-PEPTIDE AS SUBSTRATES

| Assay condition | [$^{32}$P]Peptide formed (cpm) | | |
|---|---|---|---|
| | Control | Stimulated | Blank |
| A-Kinase | 811 ± 36 | 22,025 ± 289 | 22 ± 0.6 |
| C-Kinase | 2825 ± 124 | 12,050 ± 318 | 20 ± 0.4 |

With regard to Table 1, it is noted that "Assay condition" indicates the assay mixture employed as described above, for measuring A-kinase activity with Kemptide or C-kinase activity with the GS-peptide. The stimulated condition with A-kinase was achieved with cAMP, and with C-kinase by the addition of calcium plus lipids, as described above. The enzyme source for A-kinase was the crude cytosolic extract of unstimulated adipocytes prepared according to Honnor et al (R. C. Honnor et al (1985) J. Biol. Chem. 260, 15122–15129). Since C-kinase activity in the crude cytosolic extract exhibited little stimulation by calcium plus lipid, the enzyme was partially purified as follows. After acidification to pH 5.2 with acetic acid and centrifugation to remove insoluble materials, the supernate was neutralized and diluted into a solution containing 25 mM Tris-HCl, pH 7.5, 1 mM EDTA, 1 mM EGTA, 1 mM phenylmethylsulfonyl fluoride (PMSF), 5 mM DTT, and 30% glycerol. This solution was applied to a column of DEAE-cellulose, and the C-kinase used for the above experiment was eluted by 70–100 mM NaCl. Assays were conducted for 15 min with approximately 1×10$^6$ cpm of [γ-$^{32}$P]ATP per tube, and the reactions were terminated with SDS and DTT, as described above. Samples were processed by the rapid elution method as described in the text. The final concentration of SDS in samples applied to the CM-Sephadex columns for assay of A-kinase activities was 0.1% while that for C-kinase was 0.02% (see discussion under Table 2). "Blank" represents cpm of $^{32}$P carried through the elution scheme when all assay ingredients were combined but no incubation was performed. That is, the reaction was terminated on ice immediately after addition of the enzyme sample. The "Blank" values are total cpm without subtraction of machine counting background, which was approximately 14 cpm. Values shown represent triplicate determinations (μ±SE). For the A-kinase experiment, the amount of enzyme used was of the order of 1/600 of the total in the adipocytes from the epididymal fat pads from a single rat, whereas the amount of C-kinase was approximately 1/10 of the total from an equivalent number of adipocytes. That is, in rat adipocytes, the capacity to phosphorylate Kemptide is far greater than the capacity to phosphorylate the GS-peptide.

With a wide variety of enzyme preparations, both crude and pure, the same set of CM-Sephadex and Dowex AGl-X8 columns were reused for over 100 different assays with no change in assay background or any change in recovery of phosphorylated peptides. The upper limit for the number of assay cycles that could be performed with a single set of columns was not found. The columns were repacked only to test the performance of different lots of ion exchange resins; no differences between lots were found.

Assay of protein kinase activities in crude cellular extracts. The assay of protein kinase activities, e.g. A-kinase, in extracts of adipocyte homogenates was conducted using the method of the present invention. Since fat cells are incubated in solutions containing relatively high BSA concentrations, typically 1-5%, large amounts of this exogenous protein may be introduced into the kinase reaction mixture. Assay background values increased from the usual negligible levels to approximately 100 cpm per $10^6$ cpm of [$^{32}$P]ATP upon addition of more than 600 μg of BSA to each assay tube (data not shown). Nevertheless, the columns performed satisfactorily and reproducibly from day to day if, during column regeneration, the NaCl and NaOH washes (as described above) were performed with the CM-Sephadex and Dowex AGl-X8 columns, respectively. Without these washes, background radioactivity levels continued to rise upon successive use of a given set of columns. After continued use through numerous cycles with samples containing large amounts of BSA, background radioactivity levels returned to negligible values upon subsequent assay with low amounts of exogenous protein. Finally, for routine use with all enzyme samples tested other than the BSA-laden fat cell extracts, it was not necessary to perform the NaCl and NaOH washes during regeneration of the columns.

Inclusion of SDS and a relatively high concentration of DTT nearly eliminated this high background radioactivity upon assay of A-kinase and C-kinase activities in relatively crude adipocyte samples (Table 1). In the diluted sample applied to the CM-Sephadex column, SDS concentrations as high as 0.1% did not affect recovery of phosphorylated Kemptide. However, as shown in Table 2, SDS interfered with recovery of [$^{32}$P]GS-peptide when the detergent concentration was above 0.02% in the sample applied to the CM-Sephadex column. Thus, when C-kinase assays were performed it was necessary to dilute the SDS sufficiently before applying samples to the columns.

TABLE 2

RECOVERY OF PHOSPHORYLATED SYNTHETIC PEPTIDES FROM TANDEM CHROMATOGRAPHIC COLUMNS: EFFECT OF SDS CONCENTRATION

| Peptide | Condition | Recovered (cpm)$^a$ | Recovery (%) |
|---|---|---|---|
| [$^{32}$P]Kemptide | 0.02% SDS | 14,216 ± 120 | 94 |
|  | 0.10% SDS | 14,301 ± 437 | 95 |
| [$^{32}$P]GS-Peptide | 0.02% SDS | 9,024 ± 116 | 96 |
|  | 0.10% SDS | 564 ± 29 | 6 |

It is noted that with regard to Table 2 that Kemptide and GS-peptide phosphorylated with A-kinase and C-kinase, respectively, were prepared and purified as described above. Each peptide was carried through the routine elution scheme designed for rapid processing as described in the text. Briefly, after addition of 5 ml of washing solution, samples were poured into CM-Sephadex columns, and after these columns were mounted atop the Dowex AGl-X8 columns, peptides were eluted directly into scintillation vials with 8 ml of acetic acid. The amount of [$^{32}$P]Kemptide and [$^{32}$P]GS-peptide applied was 15,060±621 and 9400±201, respectively. "Condition" refers to the SDS concentration in the sample applied to the CM-Sephadex column. This represents the final SDS concentration in the stopped reaction mix after addition of the washing solution to expand the sample volume for pouring into the column.

$^1$μ±SE; n=10

Table 3 presents a comparison between the tandem column method of the present invention with Kemptide as the substrate and the filter trap method with histone as the substrate, a method used routinely to determine A-kinase activity ratios in cellular extracts (R. C. Honnor et al, (1985) J. Biol. Chem. 260, 15122-15129). The A-kinase (−/+)cAMP activity ratios of both slightly and moderately stimulated cells were comparable in both methods, an indication of the suitability of the tandem column method for measuring activity in crude extracts. Moreover, the data in Table 3 provide a clear demonstration of the benefits in reduced background radioactivity, i.e., vastly improved signal to noise ratio. It should be noted that the background radioactivity in the filter trap method used in Table 3, approximately 400 cpm per $10^6$ cpm of substrate, is as low as the lowest values obtainable with Kemptide as the substrate when processing with phosphocellulose strips (R. Roskoski (1983) in Methods in Enzymology (J.D. Corbin and J. G. Hardman, Eds.), Vol. 99, pp. 3-6, Academic Press, New York).

TABLE 3

COMPARISON OF A-KINASE ACTIVITY RATIOS BY THE FILTER TRAP METHOD AND BY THE TANDEM CHROMATOGRAPHIC COLUMN METHOD

|  | Filter trap method $^{32}$P trapped (cpm) | | Tandem column method $^{32}$P eluted (cpm) | |
|---|---|---|---|---|
|  | 16 nM ISO | 1000 nM ISO | 16 nM ISO | 1000 nM ISO |
| Blank | 425 |  | 10 |  |
| (−) cAMP | 1282 | 2713 | 1239 | 4582 |
| (+) cAMP | 5918 | 4911 | 9385 | 8894 |
| (+) PKI | 690 | 716 | N.D. | N.D. |
| Activity ratio (−/+) cAMP | 0.113 | 0.476 | 0.132 | 0.515 |

It is noted with regard to Table 3 that A-Kinase activities were assayed as described above, with Kemptide as the substrate for processing via the tandem column method of the present invention and with histone H1 as the substrate for processing via the filter trap method (R. C. Honnor et al, (1985) J. Biol. Chem. 260, 15122-15129). Each sample was assayed for 15 min with 0.5 uCi of [γ-$^{32}$P]ATP. The enzyme sources were cytosolic extracts of adipocyte homogenates prepared according to Honnor et al (R. C. Honnor et al, (1985) J. Biol. Chem. 260, 15122-15129). Isolated rat adipocytes were incubated in the presence of 3 nM PIA and the indicated concentrations of isoproterenol (ISO) for 5 min prior to homogenization. The A-kinase inhibitor, PKI, was present where indicated at 0.6 mg/ml. N.D. refers to "Not determined" in this experiment.

As noted by Corbin (J. D. Corbin (1983) in Methods in Enzymology (J. D. Corbin and J. G. Hardman, Eds.), Vol. 99, pp. 227-232, Academic Press, New York), the use of the synthetic substrate instead of histone is advantageous with tissues containing high levels of cAMP-independent protein kinases. Previously, with the use of the specific A-kinase inhibitor, it was found that non-A-kinase activities account for 5-15% of total histone phosphorylating activity in fat cell extracts (R. C. Honnor et al, (1985) J. Biol. Chem. 260, 15122-15129). On the other hand, with Kemptide as the substrate, it has been found that non-A-kinase activities account for <5% of total Kemptide phosphorylating activity (data not shown). Thus, with the synthetic substrate, as employed in the method of the present invention, little error is introduced into A-kinase activity ratio calculations by not accounting for non-A-kinase activities, as is evident in Table 3.

After using the tandem column method of the present invention extensively for assaying both A-kinase and C-kinase in a variety of tissue samples, the only difficulty encountered was the increased background resulting from the introduction of unusually high protein concentrations in extracts of adipocyte homogenates. It should be noted that the tests performed with extraordinarily high BSA concentrations were designed to "stress" the assay system. It is evident from the data in Table 3 that A-kinase activity may be measured easily in 1/10 or 1/20 dilutions of fat cell extracts, or in greater dilutions if the radioactive substrate is increased. Although repeated use with crude samples containing relatively high protein concentrations from a variety of other sources produced no difficulties in column performance, it is possible that altered assay backgrounds might result from enzyme samples containing extremely high concentrations of proteins, either exogenous or endogenous. Since the addition of SDS and DTT to samples before boiling and loading onto the CM-Sephadex columns virtually eliminated the elevated backgrounds due to BSA, this technique is suggested for attempting to reduce protein-induced elevated background activity, should this become a problem. To determine if components of the enzyme samples are contributing to increased background radioactivity, it may be necessary to test enzyme samples occasionally in combination with the radioactive substrate both before and after performing the protein kinase incubation reaction. Also, to guard against artifacts resulting from phosphorylation of endogenous proteins which may migrate through the columns with the peptide substrates, one should perform incubations without exogenous substrates but with [$\gamma^{32}$P]ATP.

The method of the present invention offers several advantages over existing procedures. For the assay of a large number of samples, the labor-saving features may be beneficial. One need not accurately sample an aliquot of the terminated kinase reaction mix, nor is handling of individual filter strips or disks necessary. The entire sample is simply poured into a column, and the only labor involved thereafter is the addition of washing and eluting solutions to the columns with repeating syringes. Typically, one person may process 100 samples in less than 40 min. of which less than 10 min. attendance time is required; the remaining time is to allow columns to drain.

If protein kinase activity is limiting, the advantage in the method of the present invention lies in the extremely low background. Since the assay background radioactivity with the tandem-column method is lower by at least a factor of 30 than most existing methods, it follows that sensitivity in detecting kinases is increased by this same factor. Alternatively, if the kinase is not limiting, one may choose to lower the amount of radioactive substrate, [$\gamma$-$^{32}$P]ATP. For example, previously A-kinase activities were assayed with histone as the substrate, and the phosphohistone was collected on glass fiber filters (R.C. Honnor et al, J. Biol Chem. 260, (1985) pp. 15122-15129). This required the use of approximately 0.5 uCi of radioactive ATP to detect the A-kinase activity in the extracts of 1000-2000 adipocytes. With the method of the present invention, A-kinase activities in extracts of 1000 cells are easily determined with 0.05 uCi of [$\gamma^{32}$P]ATP. Also, this assay would be beneficial in detecting relatively sparse protein kinase species, such as the insulin-stimulated protein kinases in cellular extracts. Yu et al (Yu et al, J. Biol. Chem. 262, (1987) pp. 16677-16685) added 18-75 $\mu$Ci of [$\gamma$-$^{32}$P]ATP per assay tube in order to detect an insulin-stimulated serine kinase in adipocytes with Kemptide as the phosphate acceptor. With the tandem column method of the present invention, these investigators would have required 1 uCi or less of substrate for each determination, a considerable reduction in exposure to radioactivity. Finally, the cost savings resulting from a reduction in substrate may be considerable, especially for laboratories assaying large numbers of samples with several $\mu$Ci of [$\gamma$-$^{32}$P]ATP per determination, typical for many investigators in this field, or for those who require prodigious amounts of substrate.

The invention being thus described, it will be obvious the same may be varied in many ways. Such variations are not to be regarded as a departure from the spirit and scope of the invention and all such modifications as would be obvious to one skilled in the art are intended to be included within the scope of the following claims.

What is claimed is:

1. A method for separating phosphopeptides from ATP in order to subsequently measure protein kinase activity comprising the steps of:

(a) adding an amount of washing solution to a stopped reaction mixture of labelled ATP and phosphopeptides so as to form a prepared solution, wherein said washing solution is an aqueous solution containing a sufficient amount of unlabeled ATP so as to displace the labelled ATP, and said washing solution has a Ph which allows for quantitative binding of the phosphopeptides to a cation exchange resin while allowing for chemical compatibility therewith;

(b) adding said prepared solution onto a first column containing a cation exchange resin so as to absorb said phosphopeptides in said first column and remove a majority of ATP, wherein the cation exchange resin binds to said phosphopeptides and contains an ionizable, reactive group having a specific pK value such that the phosphopeptides are displaced upon eluting the cation exchange resin with an acid which has a pH lower than the pK value of said reactive group;

(c) adding an effective amount of an elution acid as defined in step (b) to said first column and collecting from said first column a first eluate of said phosphopeptides, wherein said elution acid is an acid that allows for quantitative elution of the phosphopeptides from both cation and anion exchange resins, and allows for quantitative binding of ATP to an anion exchange resin; and (d) passing said first eluate through a second column containing an anion exchange resin so as to trap residual ATP and collecting from said second column a second eluate which contains said phosphopeptides which are free from ATP, wherein said anion exchange resin is suitable for trapping residual ATP, allowing the phosphopeptides to pass thereover and contains an ionizable group which in the presence of an acid permits quantitative binding of the negatively charged phosphates of ATP, and wherein said phosphopeptides are peptides which retain a net positive charge when fully phosphorylated so as to be capable of adhering to a cation exchange resin and passing through an anion exchange resin.

2. The method of claim 1, wherein a second amount of washing solution is added to said first column after step (b) so as to remove further ATP.

3. The method of claim 1, wherein said washing solution is an aqueous solution of ATP and said elution acid is acetic acid.

4. The method of claim 1, wherein said cation exchange resin comprises a carboxymethyl derivative of a cross-linked dextran gel and said anion exchange resin comprises a cross-linked styrenedivinylbenzene matrix.

5. The method of claim 1, wherein said phosphopeptides are phosphorylated synthetic peptides.

6. The method of claim 5, wherein said member selected from the group consisting of phosphorylated Kemptide (H$_2$N-Leu-Arg-Arg-Ala-Ser-Leu-Gly-COOH) and GS peptide (H$_2$N-Pro-Leu-Ser-Arg-Thr-Leu-Ser-Val-Ala-Ala-Lys-Lys-COOH).

7. The method of claim 1, wherein prior to step (a) said stopped reaction mixture is formed as follows:
combining ATP, peptides, and protein kinase under reaction conditions so as to provide for phosphorylation of said peptides thereby forming an active reaction mixture which includes at least phosphopeptides and ATP, and
altering said reaction conditions so as to prevent further phosphorylation of said peptides thereby forming said stopped reaction mixture.

8. The method of claim 7, wherein said protein kinase is a member selected from the group consisting of A-kinase (cAMP-dependent protein kinase) and C-kinase (protein kinase C).

9. The method of claim 1, wherein said washing solution is an aqueous solution of ATP in the concentration range of from 0.5 mM to 5.0 mM with a pH in the range of 6.0 to 8.0.

10. The method of claim 1, wherein said cation exchange resin comprises a carboxymethyl derivative of a cross-linked dextran gel in the form of beads and said beads have a bead size of 40-120 microns.

11. The method of claim 1, wherein said anion exchange resin comprises a cross-linked styrene-divinylbenzene matrix in the form of beads and said beads have a size of 100-200 mesh.

12. A method for separating phosphopeptides from ATP in order to measure protein kinase activity comprising the steps of:

(a) adding an amount of washing solution to a stopped reaction mixture of radioactive ATP and phosphopeptides so as to form a prepared solution;

(b) adding said prepared solution into a first column containing a cation exchange resin so as to retain said phosphopeptides in said first column and remove a majority of ATP;

(c) adding an effective amount of an elution acid to said first column and collecting from said first column a first eluate of said phosphopeptides; and (d) passing said first eluate through a second column containing an anion exchange resin so as to trap residual ATP and collecting from said second column a second eluate which contains said phosphopeptides which are free from ATP, where the background radioactivity in said phosphopeptides free from ATP is less than 0.04% of the initial radioactivity.

13. The method of claim 12, wherein a second amount of washing solution is added to said first column after step (b) so as to remove further ATP.

14. The method of claim 12, wherein said washing solution is an aqueous solution of ATP and said elution acid is acetic acid.

15. The method of claim 12, wherein said cation exchange resin comprises a carboxymethyl derivative of a cross-linked dextran gel and said anion exchange resin comprises a cross-linked styrene-divinylbenzene matrix.

16. The method of claim 12, wherein prior to step (a) said stopped reaction mixture is formed as follows:
combining ATP, peptides, and protein kinase under reaction conditions so as to provide for phosphorylation of said peptides thereby forming an active reaction mixture which includes at least phosphopeptides and ATP, and
altering said reaction conditions so as to prevent further phosphorylation of said peptides thereby forming said stopped reaction mixture.

17. The method of claim 12, wherein said washing solution is an aqueous solution of ATP in the concentration range of from 0.5 mM to 5.0 mM with a pH in the range of 6.0 to 8.0.

18. The method of claim 12, wherein said cation exchange resin comprises a carboxymethyl derivative of a cross-linked dextran gel in the form of beads and said beads have a bead size of 40-120 microns.

19. The method of claim 12, wherein said anion exchange resin comprises a cross-linked styrene-divinylbenzene matrix in the form of beads and said beads have a size of 100-200 mesh.

* * * * *